United States Patent [19]

Meyer et al.

[11] Patent Number: 4,521,429
[45] Date of Patent: Jun. 4, 1985

[54] VINYLAZOLES AND THEIR USE FOR CONTROLLING FUNGI

[75] Inventors: Norbert Meyer, Ladenburg; Bernd Zeeh; Ernst Buschmann, both of Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 342,933

[22] Filed: Jan. 26, 1982

[30] Foreign Application Priority Data

Jan. 30, 1981 [DE] Fed. Rep. of Germany ....... 3103068

[51] Int. Cl.³ .................... A01N 43/50; A01N 43/64; C07D 233/60; C07D 249/08
[52] U.S. Cl. .................... 514/383; 514/184; 514/396; 548/101; 548/262; 548/335
[58] Field of Search .................. 548/101, 262, 335; 542/458; 424/269, 245, 273 R

[56] References Cited

U.S. PATENT DOCUMENTS 4,085,209 4/1978 Miller et al. .................. 548/335
4,086,351 4/1978 Balasubramanyan et al. ..... 548/262
4,104,399 8/1978 Pommer et al. ................ 424/269
4,213,990 7/1980 Frick et al. ................... 424/269
4,315,017 2/1982 Linhart et al. ................ 424/269
4,357,340 11/1982 Thorogood ................... 424/273 R

OTHER PUBLICATIONS

Bourgeois et al., J. Heterocycl. Chem., vol. 15, pp. 1543-1545, (1978).

Primary Examiner—Alton D. Rollins
Attorney, Agent, or Firm—Keil & Weinkauf

[57] ABSTRACT

Vinylazoles of the formula

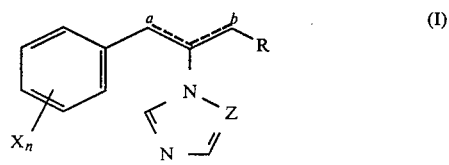

where X, Z, R and n have the meanings given in the description and the double bond is in position a or b, and their use for controlling fungi.

12 Claims, No Drawings

VINYLAZOLES AND THEIR USE FOR CONTROLLING FUNGI

The present invention relates to vinylazoles, fungicides containing these compounds as active ingredients, and a method of controlling fungi using these compounds.

German Laid-Open Application DOS No. 2,645,617 discloses that vinylazoles have a fungicidal action.

We have found that vinylazoles of the formula

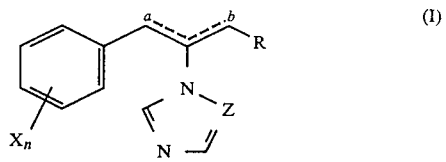

where R is hydrogen, alkyl of 1 to 7 carbon atoms, phenyl or halogen-substituted phenyl, X is hydrogen, halogen, alkyl of 1 to 4 carbon atoms or phenyl, Z is N or CH and n is an integer from 1 to 5, and the double bond occupies either position a or position b, and plant-tolerated acid addition salts and metal complexes thereof, have a superior fungicidal activity to known vinylazoles.

The compounds of the formula I can exist as E/Z isomers. The term vinylazoles accordingly means both the pure isomers and their mixtures.

Mixtures of compounds of the formula I which are identical in respect of R, X, Z and n, but in which the position of the double bond differs, can be formed in the preparation of the vinylazoles of the formula I. These mixtures are included in formula I; in their definition, the position of the double bond is given as a/b.

In formula I, R is hydrogen, straight-chain or branched alkyl of 1 to 7 carbon atoms, eg. methyl, ethyl, isopropyl, n-propyl, tert.-butyl, n-butyl, n-pentyl, n-hexyl or n-heptyl, or phenyl which can be monosubstituted or polysubstituted by halogen, eg. chlorine or bromine, such as 4-chlorophenyl, 2,4-dichlorophenyl or 4-bromophenyl. X in formula I is hydrogen, phenyl, halogen, eg. chlorine, bromine or iodine, or straight-chain or branched alkyl of 1 to 4 carbon atoms, eg. methyl, ethyl, n-propyl, sec.-butyl, isobutyl or tert.-butyl.

Preferred compounds of the formula I are those where R is alkyl, the double bond occupies position a or b and $X_n$ is, for example, 2-chloro, 4-bromo, 2,4-dichloro, 4-methyl or 4-phenyl.

The vinylazoles of the formula I are obtained by eliminating HY from a compound of the formula

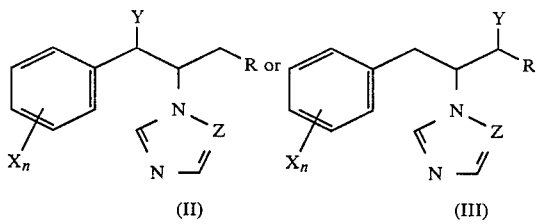

where R, X, Z and n have the above meanings and Y is a leaving group.

Suitable leaving groups Y are hydroxyl, tosylate, mesylate, halide, acetate, trifluoroacetate and xanthate.

If Y is hydroxyl, the vinylazoles of the formula I are obtained by eliminating water from a corresponding α-azolylalcohol of the formula II or III in the presence of an acidic dehydrating catalyst, such as a proton acid, Lewis acid, acid anhydride or acid chloride, eg. sulfuric acid, phosphoric acid, formic acid, p-toluenesulfonic acid, boron trifluoride, diphosphorus pentoxide, acetic anhydride, phosphorus oxychloride or thionyl chloride.

The amount of acid catalyst is from 10 to 200% by weight of the α-azolylalcohol.

The elimination of water is carried out at from 70° to 180° C., preferably from 80° to 120° C., in the presence or absence of a solvent. A solvent is preferably used.

Suitable solvents are toluene, xylene, pyridine, glacial acetic acid and acetonitrile.

The hydroxyl group can also be converted into a more readily detachable group, for example into a tosylate, halide or acetate group. This leaving group can then be split off in the presence of a basic catalyst, eg. an alcoholate, a tertiary amine, an alkali metal carbonate, such as sodium methylate, sodium ethylate, potassium tert.-butylate, pyridine or potassium carbonate, or in the presence of sodium sulfide at from 20° to 100° C.

From 1 to 2.5 moles of basic catalyst are used per mole of compound of the formula II or III.

The elimination reaction is preferably carried out in the presence of a solvent. Suitable solvents are aliphatic alcohols, eg. ethanol, n-butanol, tert.-butanol and octanol, chlorohydrocarbons, eg. chloroform and methylene chloride, N,N-dialkylamides, eg. dimethylformamide, and dimethylsulfoxide, pyridine, toluene, tetrahydrofuran and water. Mixtures of these solvents can also be used.

The hydroxyl group can also be esterified, ie. converted into an acetate or xanthate group, which can then be eliminated by heating in a conventional manner (Houben-Weyl, Methoden der organischen Chemie, Volume 5/1b, page 109 et seq., Georg Thieme-Verlag, Stuttgart, 1972).

The vinylazoles of the formula I can be converted to plant-tolerated salts or metal complexes in a conventional manner. Mineral acids, eg. hydrochloric acid, hydrobromic acid, sulfuric acid, nitric acid and phosphoric acid, and organic acids, eg. acetic acid and dodecylbenzenesulfonic acid, are suitable for salt formation. The fungicidal activity of the salts of the vinylazoles is based on the cation, so that any desired anion can be chosen from the large number of plant-tolerated anions.

Metal complexes can be formed by adduct formation from a vinylazole and the cation of a metal salt. Copper, zinc, iron, manganese and nickel salts are particularly suitable, eg. copper-II chloride, copper-II sulfate, copper-II nitrate, zinc-II chloride, iron-III chloride, manganese-II chloride and nickel-II bromide.

The compounds of the formulae II and III, used as starting materials, where Y is hydroxyl can be prepared from an α-azolyl ketone in a conventional manner (German Laid-Open Application DOS No. 2,734,426).

The Examples which follow illustrate the preparation of the novel compounds.

EXAMPLE 1

1-(2,4-Dichlorophenyl)-4,4-dimethyl-2-(1,2,4-triazol-1-yl)-pent-1-ene 49.2 g of 1-(2,4-dichlorophenyl)-4,4-dimethyl-2-(1,2,4-triazol-1-yl)-pentan-3-ol (in the form of a diastereomer mixture) were dissolved in 500 ml of absolute tetrahydrofuran, and 6.0 g of an 80% strength dispersion of sodium hydride were added at room temperature, whilst stirring. The mixture was stirred at from 40° to 50° C. for eight hours and was cooled to room temperature. A solution of 28.2 g of toluene-4-sulfonyl chloride in 60 ml of absolute tetrahydrofuran was then added dropwise, the mixture was stirred for a further 12 hours at room temperature, hydrolyzed with water and extracted several times with 500 ml of methylene chloride, and the organic phase was then dried over sodium sulfate and concentrated. Fractional crystallization of the residue from ethyl acetate gave 42.5 g of the diastereomeric tosylates. The product was dissolved in 500 ml of dimethylsulfoxide, and 54 g of ground sodium sulfide were added. The mixture was stirred at room temperature for one hours, 1 l of water was added, the mixture was extracted twice with 1 l of diethyl ether each time and the organic phase was dried over sodium sulfate and concentrated. The oily residue was taken up in a little ethanol and the mixture was cooled; 4.5 g of 1-(2,4-dichlorophenyl)-4,4-dimethyl-2-(1,2,4-triazol-1-yl)-pent-1-ene of melting point 133° C. crystallized out (isomer A). Concentration of the mother liquor gave 14.0 g of 1-(2,4-dichlorophenyl)-4,4-dimethyl-2-(1,2,4-triazol-1-yl)-pent-1-ene of boiling point 132°–138° C./0.05 mbar as an oil (isomer B).

EXAMPLE 2

1-(2,4-Dichlorophenyl)-2-(1,2,4-triazol-1-yl)-pent-2-ene 42.9 g of thionyl chloride were added dropwise to a solution of 107 g of 1-(2,4-dichlorophenyl)-2-(1,2,4-triazol-1-yl)-pent-1-anol in 500 ml of chloroform at room temperature, and the mixture was stirred for 12 hours and then refluxed for 4 hours. It was washed with water, sodium bicarbonate solution and water in succession, and the organic phase was dried over sodium sulfate and concentrated. The crude product was dissolved in diethyl ether, and 34 g of the nitrate of 1-(2,4-dichlorophenyl)-2-(1,2,4-triazol-1-yl)-1-chloropentane of melting point 127° C. were precipitated with nitric acid. The product was stirred with 30.2 g of potassium tert.-butylate in 400 ml of tert.-butanol at room temperature for 7 hours. The mixture was then concentrated, the residue was taken up in chloroform, the mixture was washed with water, the organic phase was dried over sodium sulfate and the solvent was stripped off by distillation to give 10 g of 1-(2,4-dichlorophenyl)-2-(1,2,4-triazol-1-yl)-pent-2-ene of boiling point 140°–144° C./0.1 mbar.

The following vinylazoles of the formula I, for example, were prepared in a similar manner.

| No. | R | $X_n$ | Z | Position of the double bond | M.p./B.p. [°C.] |
|---|---|---|---|---|---|
| 3 | tert.-$C_4H_9$ | 4-Cl | N | a | 78–90 |
| 4 | tert.-$C_4H_9$ | 4-Br | N | a | 133–140 |
| 5 | tert.-$C_4H_9$ | 4-$CH_3$ | N | a/b | 52–59 |
| 6 | tert.-$C_4H_9$ | H | N | a/b | 110–112/0.2 mbar |
| 7 | tert.-$C_4H_9$ | 4-$C_6H_5$ | N | a | 92–98 |
| 8 | n-$C_3H_7$ | 2-Cl, 4-Cl | N | a/b | 152–156/0.13 mbar |
| 9 | $C_2H_5$ | 2-Cl, 4-Cl | CH | a/b | 170–190/0.4 mbar |
| 10 | tert.-$C_4H_9$ | 2-Cl, 4-Cl | CH | a | 135/0.01 mbar |
| 11 | i-$C_3H_7$ | 2-Cl, 4-Cl | N | a/b | 148–152/0.08 mbar |
| 12 | tert.-$C_4H_9$ | 2-I | N | a/b | resin |
| 13 | tert.-$C_4H_9$ | 2-Cl, 4-Cl, 6-Cl | N | a/b | resin |
| 14 | tert.-$C_4H_9$ | 2-I, 6-I | N | a/b | resin |
| 15 | H | 2-Cl, 4-Cl | N | a/b | oil |
| 16 | H | 2-Cl, 4-Cl | CH | a/b | oil |
| 17 | n-$C_5H_{11}$ | 2-Cl, 4-Cl | N | a/b | oil |
| 18 | n-$C_6H_{13}$ | 2-Cl, 4-Cl | N | a/b | oil |
| 19 | 2,4-Dichlorophenyl | 2-Cl, 4-Cl | N | a | resin |
| 20 | 2,4-Dichlorophenyl | 2-Cl, 4-Cl | CH | a | resin |
| 21 | 4-Chlorophenyl | 2-Cl, 4-Cl | N | a/b | resin |

The new active ingredients have a strong fungitoxic action on phytopathogenic fungi, especially from the Ascomycetes class, e.g., *Erysiphe graminis* in wheat, *Erysiphe cichoriacearum* in cucumbers, *Uncinula necator* in grapes, *Podosphaera leucotricha* and *Venturia inaequalis* in apples, and *Botrytis cinerea* in grapes.

The new compounds may also be used for protecting materials, e.g., against attack by molds such as *Trichoderma viride*, wood-rot fungi such as *Chaetomium globosum*, or by wood-destroying fungi such as *Coniophora cerebella* and *Polystictus versicolor*.

The fungicidal agents employed contain from 0.1 to 95, and preferably from 0.5 to 90, wt% of active ingredient. The application rates depend on the type of effect desired, and vary from 0.01 to 3 kg and more, but preferably from 0.01 to 1 kg of active ingredient per hectare.

The agents are applied for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such as dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfonates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of formulations are given below.

I. 90 parts by weight of the compound of Example 1 is mixed with 10 parts by weight of N-methyl-α-pyrrolidone. A mixture is obtained which is suitable for application in the form of very fine drops.

II. 20 parts by weight of compound 5 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil. By pouring the solution into water and finely distributing it therein, an aqueous dispersion is obtained.

III. 20 parts by weight of compound 3 is dissolved in a mixture consisting of 640 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil. By pouring the solution into water and finely distributing it therein, an aqueous dispersion is obtained.

IV. 20 parts by weight of compound 3 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide with 1 mole of castor oil. By pouring the solution into water and finely distributing it therein, an aqueous dispersion is obtained.

V. 80 parts by weight of compound 10 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By finely distributing the mixture in water a spray liquor is obtained.

VI. 5 parts by weight of compound 11 is intimately mixed with 95 parts by weight of particulate kaolin. A dust is obtained containing 5% by weight of the active ingredient.

VII. 30 parts by weight of the compound of Example 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 4 is intimately mixed with 10 parts of the sodium salt of a phenolsulfonic acid-urea-formadlehyde condensate, 2 parts of silica gel and 48 parts of water. Dilution in water gives an aqueous dispersion.

IX. 20 parts of compound 7 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may also be mixed with other, prior art, fungicides; in many cases the fungicidal spectrum of action is broadened. With a number of these fungicidal compositions synergistic effects occur, i.e., the fungicidal action of the combination is greater than that of its components added together.

Examples of fungicides which can be combined with the compounds of the invention are: dithiocarbamates and their derivatives, e.g. iron(III)dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazone)-3-methyl-5-isoxazolone, pyridine-2-thio-1-oxide, 8-hyroxyquinoline and its copper salt, 2,3-dihydro-5-carboxanilido-6-methyl-1,4-oxathiin-4,4-dioxide, 2,3-dihydro-5-carboxanilido-6-methyl-1,4-oxathiin, 2-fur-2-yl-benzimidazole, piperazine-1,4-diyl-bis-(1-(2,2,2-trichloroethyl)-forma mide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodobenzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclodecyl-morpholine and its salts, diisopropyl 5-nitroisophthalate, 1-(1',2',4'-triazol-1'-yl)-(4'-chlorophenoxy)-3,3-dimethylbutan-2-one, 1-(1',2',4'-triazol-1'-yl)-(4'-chlorophenoxy)-3,3-dimethylbutan-2-ol, N-(n-propyl)-N-(2,4,6-trichlorophenoxyethyl)-N'-imidazolylurea, N-cyclohexyl-N-methoxy-2,5-dimethylfuran-3-carboxamide, 2,4,5-trimethyl-furan-3-carboxanilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, and N-[3-(p-tert-butylphenyl)-2-methyl-propyl]-cis-2,6-dimethylmorpholine.

The following examples demonstrate the biological action of the novel compounds of the formula I. The prior art fungicidal active ingredient 1-(1,2,4-triazol-1-yl)-1-(p-chlorophenacyl)-styrene (German Laid-Open Application DOS No. 2,645,617) was used for comparison purposes.

EXAMPLE A

Action on wheat mildew

Leaves of pot-grown wheat seedlings of the "Jubilar" variety were sprayed with aqueous emulsions, the solids of which consisted of 80% (by weight) of active ingredient and 20% of emulsifier, and dusted, after the sprayed-on layer had dried, with spores of wheat mildew (Erysiphe graminis var. tritici). The plants were then placed in a greenhouse at 20° to 22° C. and 75 to 80% relative humidity. The extent of mildew spread was determined after 10 days.

In this experiment, compounds nos. 3, 9 and 10, and isomers A and B of compound no. 1 (Example 1), had a good action.

EXAMPLE B

Action on Erysiphe cichoriacearum in cucumbers

Leaves of pot-grown cucumber seedlings were sprayed with aqueous emulsions, the solids comprising 80% of active ingredient and 20% of emulsifier, and dusted, after the sprayed-on layer had dried, with spores of cucumber mildew (Erysiphe cichoriacearum). The plants were then placed in a greenhouse at from 20° to 22° C. and from 75 to 80% relative humidity. The extent of fungus development was determined after 10 days.

In this experiment, active ingredients nos. 3, 9 and 10, and isomers A and B of compound no. 1 (Example 1), had a better fungicidal action than the prior art active ingredient.

EXAMPLE C

Action on Botrytis cinerea in pimientos

Pimiento seedlings of the "Neusiedler Ideal Elite" variety were sprayed, after 5 leaves were well developed, to runoff with 0.05 wt% aqueous suspensions containing (dry basis) 80% of active ingredient and 20% of sodium ligninsulfonate. After the sprayed-on layer had dried, the plants were sprinkled with a conidial suspension of the fungus Botrytis cinerea, and placed at 22° to 24° C. in a chamber of high humidity to obtain optimum conditions for promoting fungus growth. After 5 days, the disease had spread to such a great extent on the untreated plants that the necroses covered the major portion of the leaves.

In this test, both isomers A and B of compound 1 (Example 1) and compound 3 had a very good action.

We claim:

1. Vinylazoles of the formula

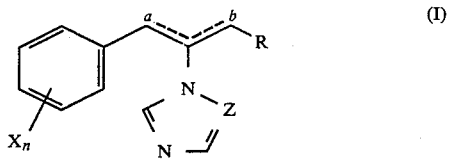

where R is alkyl of 1 to 7 carbon atoms, phenyl or halogen-substituted phenyl where the double bond occupies position b and is n-propyl, isopropyl, tert.-butyl, n-butyl, n-pentyl, n-hexyl, n-heptyl, phenyl or halogen substituted phenyl where the double bond occupies position a, X is hydrogen, halogen, alkyl of 1 to 4 carbon atoms or phenyl, Z is N or CH and n is an integer from 1 to 5, and plant-tolerated acid addition salts and metal complexes thereof.

2. Vinylazoles of the formula I as defined in claim 1, wherein R is tert.-butyl and the double bond occupies position a.

3. Vinylazoles of the formula

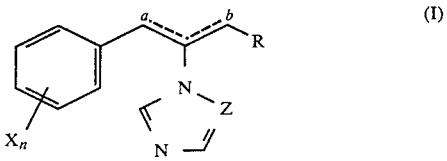

where R is alkyl of 1 to 7 carbon atoms, phenyl or halogen-substituted phenyl, X is hydrogen, halogen, alkyl of 1 to 4 carbon atoms or phenyl, Z is N or CH and n is an integer from 1 to 5, and the double bond occupies the position b, and plant-tolerated acid addition salts and metal complexes thereof.

4. Vinylazoles of the formula

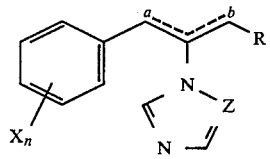 (I)

where R is n-propyl, isopropyl, tert.-butyl, n-butyl, n-pentyl, n-hexyl or n-heptyl, X is hydrogen, halogen, alkyl of 1 to 4 carbon atoms or phenyl, Z is N or CH and n is an integer from 1 to 5, and the double bond occupies position a, and plant tolerated acid addition salts and metal complexes thereof.

5. Vinylazoles of the formula I as defined in claim 1, wherein Z is N.

6. A vinylazole of the Formula I as defined in claim 10 wherein X is 4-Br, Z is N, R is tert. butyl and the double bond occupies the a position.

7. 1-(2,4-Dichlorophenyl)-4,4-dimethyl-2-[1-(1,2,4-triazolyl)]-pent-1-ene.

8. 1-(4-Chlorophenyl)-4,4-dimethyl-2-[1-(1,2,4-triazolyl)]-pent-1-ene.

9. Vinylazoles of the formula I, as set forth in claim 4 wherein $X_n$ is 2-chloro, 4-bromo, 2,4-dichloro, 4-methyl or 4-phenyl.

10. Vinylazoles of the formula (I), as set forth in claim 3, wherein R is alkyl of 1 to 7 carbon atoms.

11. A fungicidal agent containing inert additives and a fungicidally effective amount of a vinylazole of the formula I as defined in claim 1.

12. A process for combating fungi, wherein a fungicidally effective amount of a vinylazole of the formula I as defined in claim 1 is allowed to act on the fungi, or materials, areas, plants or seed threatened by fungus attack.

* * * * *